United States Patent [19]

Cox et al.

[11] 4,006,230
[45] Feb. 1, 1977

[54] 7-D-(α-ACYLAMINO-ARYLACETAMIDO)-CEPHALOSPORANIC ACID DERIVATIVES

[75] Inventors: David A. Cox; Braham Shroot, both of Canterbury, England

[73] Assignee: Pfizer Inc., New York, N.Y.

[22] Filed: Nov. 26, 1975

[21] Appl. No.: 635,297

Related U.S. Application Data

[63] Continuation-in-part of Ser. No. 504,381, Sept. 9, 1974, abandoned.

[30] Foreign Application Priority Data

Sept. 13, 1973 United Kingdom ............ 43033/73

[52] U.S. Cl. .......................... 424/246; 260/243 C; 260/326 R; 260/475 SC; 260/4 PS
[51] Int. Cl.² ............. C07D 501/24; C07D 501/32
[58] Field of Search ................. 260/243 C; 424/246

[56] References Cited

UNITED STATES PATENTS 3,341,532  9/1967  Lewis et al. ................... 260/243 C

OTHER PUBLICATIONS

Heusler et al., "Chemical Abstracts," 23-12-71, vol. 76, p. 460, Abst. No. 99691e.

*Primary Examiner*—Nicholas S. Rizzo
*Assistant Examiner*—David E. Wheeler
*Attorney, Agent, or Firm*—Connolly and Hutz

[57] ABSTRACT

Novel antibacterial agents; namely, 7-(α-acylamino-arylacetamido)-cephalosporanic acid derivatives having the formula:

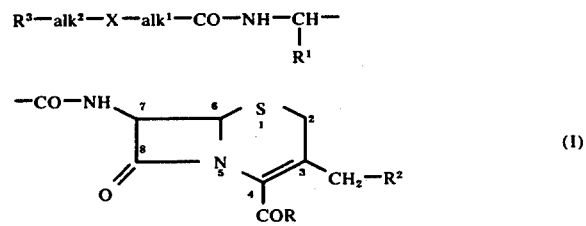

wherein $R^1$ is thienyl, 2-furyl, phenyl, substituted thienyl or substituted phenyl; R is hydroxyl; $R^2$ is hydrogen, hydroxy, acetoxy, carbamoyloxy, N-pyridyl, azido or heterocyclic thio group; R and $R^2$ when taken together represent an oxygen atom; $R^3$ is sulpho or $COOR^{4'}$ wherein $R^{4'}$ is hydrogen or $R^4$ wherein $R^4$ is lower alkyl, 5-indanyl, naphthyl, phenyl, or substituted phenyl, $CONR^5R^6$, wherein each of $R^5$ and $R^6$ is hydrogen, lower alkyl or cycloalkyl; or $R^5$ and $R^6$ together with the nitrogen atom to which they are attached form a saturated heterocyclic group; X is oxygen or sulphur, a direct link, carbonyl, methylene, hydroxymethylene, sulphinyl, sulphonyl or an imino group of the formula —$NR^7$—, wherein $R^7$ is hydrogen, lower alkyl, lower alkenyl, or benzyl; and each of $alk^1$ and $alk^2$ is a divalent saturated aliphatic hydrocarbon group containing from 1 to 3 carbon atoms; the pharmaceutically acceptable salts thereof, and methods for their preparation.

18 Claims, No Drawings

7-D-(α-ACYLAMINO-ARYLACETAMIDO)-CEPHALOSPORANIC ACID DERIVATIVES

CROSS-REFERENCE TO RELATED APPLICATION

This application is a continuation-in-part of application Ser. No. 504,381, now abandon, filed Sept. 9, 1974.

BACKGROUND OF THE INVENTION

The invention relates to antibacterial agents and is particularly concerned with a class of novel cephalosporin derivatives with broad spectrum antibacterial activity, more especially against gram-negative organisms. In particular, the compounds of the invention constitute a series of 7-(α-aminoarylacetamido)-Δ$^3$-cephem derivatives having a novel type of acyl group attached to the α-amino group.

British Pat. No. 1,328,340, published Aug. 30, 973, describes cephalosporins having the above formula wherein X is a direct carbon-carbon link or a methylene group. However, such compounds as are claimed in the present invention are not structurally obvious over these prior art compounds. Additionally, they exhibit superior antibacterial activity relative to the prior art compounds.

SUMMARY OF THE INVENTION

According to the invention, there are provided compounds having the general formula:

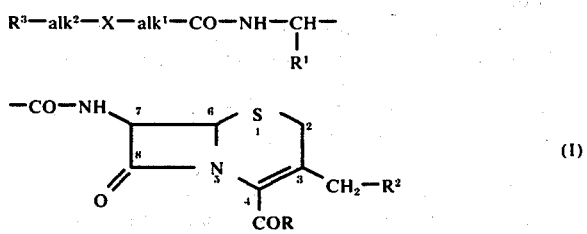

wherein $R^1$ represents a phenyl, 2- or 3-thienyl or 2-furyl group, the phenyl and thienyl groups optionally being substituted with one or more moieties chosen from halogen, hydroxyl, lower alkyl, lower alkoxy and trifluoromethyl; R represents a hydroxyl group, and $R_2$ represents a hydrogen atom or a hydroxy, acetoxy, carbamoyloxy, N-pyridyl, substituted N-pyridyl, azido or heterocyclicthio group, for example, a 4,6-dimethyl pyrimidin-2-ylthio, 4,5-dimethylthiazol-2-ylthio, 1,3,5-triazin-2-ylthio, pyrimidin-2-ylthio, 2-methyl-1,3,4-thiadiazol-5-ylthio, 2-methyl-1,3,4-oxadiazol-5-ylthio or 1-substituted-1,2,3,4-tetrazol-5-ylthio group wherein the 1-substituent represents a lower alkyl, lower alkenyl, cycloalkyl, benzyl or phenyl group, the latter group optionally being substituted with one or more moieties chosen from halogen, lower alkyl and lower alkoxy; or R and $R^2$ taken together represent an oxygen atom; $R^3$ represents a sulpho group; or a group of the formula COOR$^{4'}$, wherein R$^{4'}$ represents hydrogen or $R^4$ wherein $R^4$ is lower alkyl, 5-indanyl, naphthyl or phenyl group, the phenyl group optionally being substituted with one or more moieties chosen from halogen, lower alkyl, lower alkoxy and trifluoromethyl; or a carbamoyl group of the formula CONR$^5$R$^6$, wherein R$^5$ and R$^6$ each independently represent a hydrogen atom or a lower alkyl or a cycloalkyl group, or together with the nitrogen atom to which they are attached form a saturated heterocyclic group; X represents an oxygen or sulphur atom, a direct carbon-carbon link, or a carbonyl, methylene, hydroxymethylene, sulphinyl or sulphonyl group, or an imino group of the formula —NR$^7$—, wherein R$^7$ represents a hydrogen atom or a lower alkyl, lower alkenyl, or a benzyl group; and alk$^1$ and alk$^2$ each independently represent a divalent saturated aliphatic hydrocarbon group containing from 1 to 3 carbon atoms; and the pharmaceutically acceptable salts thereof.

The pharmaceutically acceptable salts of the novel compounds of the invention include non-toxic metallic salts, particularly of lithium, sodium, potassium, calcium and aluminum, ammonium, and substituted ammonium salts, e.g., of trialkylamines, N-ethylpiperidine, procaine, dibenzylamine, N-benzyl-β-phenylethylamine, 1-ephenamine, N,N'-dibenzylethylenediamine, dehydroabietylamine, N,N'-bis-dehydroabietylethylenediamine and other amines previously used to form salts with benzylpenicillin. Compounds of the formula (I) in which $R^2$ represents an N-pyridyl group, itself positively charged, are internal salts, having the 4-carboxyl group converted to the corresponding carboxy anion, COO$^-$.

In the above-described normal salts, a single cation may accompany the terminal deprotonated carboxyl or sulpho group represented by $R^3$, or the deprotonated 4-carboxyl group, or there may be two cations, one accompanying each of the deprotonated groups.

In this specification, by "halogen" is meant fluorine, chlorine, bromine, or iodine and the term "lower" applied to an alkyl, alkoxy or alkenyl group indicates that such a group contains up to 6 carbon atoms. Where a lower alkyl, alkoxy or alkenyl group contains from 3 to 6 carbon atoms, it may be straight or branched chain. A cycloalkyl group may contain from 3 to 6 carbon atoms.

When $R^3$ in the formula (I) represents a carbamoyl group of the formula CONR$^5$R$^6$, any saturated heterocyclic group represented by NR$^5$R$^6$ may contain a second nitrogen atom or an oxygen or sulphur atom as a ring atom. A second nitrogen atom preferably carries a lower alkyl or a benzyl group as substituent. Examples of saturated heterocyclic groups embraced by NR$^5$R$^6$ are the pyrrolidino, piperidino, morpholino, thiomorpholino, perhydroazepino, piperazino or perhydrodiazepino groups, the latter two preferably bearing a lower alkyl or a benzyl group on the second nitrogen atom.

The divalent saturated aliphatic hydrocarbon group represented by alk$^1$ and alk$^2$ may have the free valencies located on the same or different carbon atoms. Hence, each may be a methylene, ethylene, trimethylene, ethylidene, propylidene, or 1- or 2-methylethylene group.

The cephalosporin derivatives of the present invention are capable of existing in epimeric "D" and "L" forms, and the invention includes the separated D- and L-epimers as well as mixtures thereof.

One preferred group of compounds of formula (I) are those in which R is a hydroxy group;

$R^1$ represents a phenyl, 2-thienyl or 2-furyl group, the first two groups optionally being substituted with one or more moieties chosen from halogen, hydroxyl, lower alkyl, lower alkoxy and trifluoromethyl;

$R^2$ represents a hydrogen atom or an acetoxy, unsubstituted N-pyridyl, substituted N-pyridyl, azido, 2- methyl-1,3,4-thiadiazol-5-ylthio, 2-methyl-1,3,4-oxadiazol-5-ylthio or 1-substituted-1,2,3,4-tetrazol-5-ylthio group wherein the 1-substituent represents a lower alkyl, lower alkenyl, cycloalkyl, benzyl or phenyl group, the latter group optionally being substituted with one or more moieties chosen from halogen, lower alkyl and lower alkoxy;

$R^3$ is as previously defined for formula (I);

X represents an oxygen or sulphur atom, a direct carbon-carbon link, or a carbonyl, methylene, hydroxymethylene, sulphinyl or sulphonyl group, or an imino group of the formula —$NR^4$—, wherein $R^7$ represents a hydrogen atom or a lower alkyl or a benzyl group; and $alk^1$ and $alk^2$ are as defined for formula (I);

and the pharmaceutically acceptable salts thereof.

More preferably, the invention provides compounds of the formula (I) wherein R is a hydroxy group, $R^1$ represents a phenyl group optionally substituted with one or more moieties chosen from halogen, hydroxyl, lower alkyl, lower alkoxy and trifluoromethyl; $R^2$ represents an acetoxy or 1-substituted-1,2,3,4-tetrazol-5-ylthio group wherein the substituent is as defined for formula (I); $R^3$ represents a carboxyl group or an ester group of the formula —$COOR^4$ wherein $R^4$ is as defined for formula (I); X is an oxygen atom; and $alk^1$ and $alk^2$ are each a methylene group.

Preferably $R^1$ is a p-hydroxyphenyl group optionally substituted with one or more moieties chosen from halogen, lower alkyl, lower alkoxy and trifluoromethyl, and most preferably is a p-hydroxyphenyl or m-chloro-p-hydroxyphenyl group.

Particularly preferred individual compounds include the following:

7-D-(α-carboxymethoxyacetamido-phenylacetamido(-cephalosporanic acetamido-phenylacetamido)cephalosporanic acid;

7-D-(α-Carboxymethoxyacetamido-phenylacetamido)-3-(1-methyl-1,2,3,4-tetrazol-5-ylthiomethyl)-Δ³-cephem-4-carboxylic acid;

7-D-(α-Carboxymethoxyacetamido-phenylacetamido)-3-(2-methyl-1,3,4-thiadiazol-5-ylthiomethyl)-Δ³-cephem-4-carboxylic acid;

7-D-(α-Carboxymethoxyacetamido-[p-hydroxphenyl]acetamido)cephalosporanic acid;

7-D-(α-Carboxymethoxyacetamido-[m-chloro-p-hydroxyphenyl]acetamido)-cephalosporanic acid;

7-D-(α-Carboxymethoxyacetamido-[p-hydroxyphenyl]acetamido)-3-(1-methyl-1,2,3,4-tetrazol-5-ylthiomethyl)-Δ³-cephem-4-carboxylic acid;

7-D-(α-Carboxymethoxyacetamido-[m-chloro-p-hydroxyphenyl]acetamido)-3-(1-methyl-1,2,3,4-tetrazol-5-ylthiomethyl)-Δ³-cephem-4-carboxylic acid;

7-D-(α-Carboxymethyl-[N-methyl]aminoacetamido-phenylacetamido)-3-(1-methyl-1,2,3,4-tetrazol-5-ylthiomethyl)-Δ³-cephem-4-carboxylic acid;

7-D-(α-[5-Indanyl]oxycarbonylmethoxyacetamido-phenylacetamido-cephalosporanic acid;

7-D-(α-Isopropylphenyl]oxycarbonylmethoxyacetamido-phenylacetamido)cephalosporanic acid;

7-D-(α-[2-Methoxyphenyl]oxycarbonylmethoxyacetamido-phenylacetamido)cephalosporanic acid;

7-D-(α-[2-Methylphenyl]oxycarbonylmethoxyacetamido-phenylacetamido)-cephalosporanic acid; and 7-D-(α-[n-butyl]oxycarbonylmethoxyacetamido-phenylacetamido)cephalosporanic acid.

DETAILED DESCRIPTION OF THE INVENTION

The compounds of the invention may be prepared in a number of ways, including the following:

1. Compounds of the formula (I), in which $R^3$ represents a carboxyl or sulpho group, $R^2$ is as already defined other than a hydroxy group, and X is as already defined other than an unsubstituted imino group, —NH—, may be prepared by reacting a 7-(α-aminoarylacetamido)-4-carboxy-Δ³-cephem derivative of the formula:

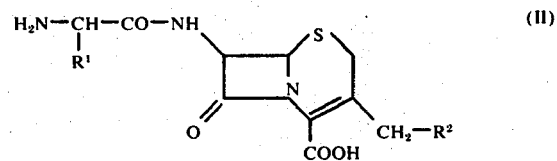

with a cyclic anhydride of the formula:

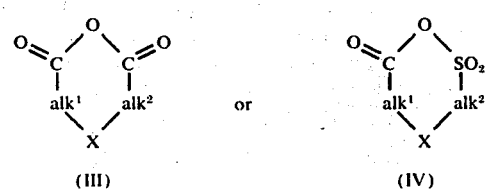

respectively, wherein X is defined as above in this method.

Such a reaction may be accomplished by mixing together the reagents, that of the formula (II) optionally as a salt or necessarily as an internal salt in the case where $R^2$ represents an N-pyridyl group, in a reaction-inert organic solvent medium, e.g. dimethylformamide, methylene dichloride or acetone, optionally containing a tertiary amine base, e.g. triethylamine or pyridine, or an inorganic base, e.g. sodium bicarbonate. Generally, the reaction goes substantially to completion during a period from ½ to 12 hours when the mixture is maintained within the temperature range 10°-45° C., preferably with stirring. Isolation of the product is typically achieved by extracting the reaction mixture with an aqueous medium, e.g. water itself or a basic aqueous medium such as saturated aqueous sodium bicarbonate solution, overlayering the separated aqueous medium with a suitable water-immiscible solvent, e.g. ethyl acetate, acidifying the aqueous phase, e.g. by addition of a mineral acid such as hydrochloric acid and shaking the two-phase solution in order to extract the product into the organic phase, and thereafter separating, washing (e.g. with a saline solution), drying (e.g. with anhydrous magnesium or sodium sulphate), filtering and evaporating to dryness the organic phase. If necessary, the product may be purified by a standard recrystallization technique.

In the case of compounds of the formula (I) in which the grouping $alk^2$-X-$alk^1$ represents or embraces a hydrocarbon chain containing 4 or more carbon atoms, the reaction involving a cyclic anhydride of the formula (III) is generally performed using that compound in a polymeric form in view of the frequent difficulty in obtaining it in a monomeric form. An isolation procedure similar to the one described above would frequently afford a product contaminated with a significant quantity of dicarboxylic acid of the formula:

HOOC—alk$^2$—X—alk$^1$—COOH   (V)

and accordingly it is often necessary to perform more than a single acidification-extraction step at different degrees of acidity and investigate the nature of the extracted product at each stage in order to isolate the desired product in an acceptable state of purity.

2. A half-ester of the formula:

R$^4$OOC—alk$^2$—X—alk$^1$—COOH   (VI)

wherein X represents any of the hereinbefore specified atoms or groups with the exception of an unsubstituted imino group, —NH—, and which itself may be prepared according to conventional procedures involving reacting the appropriate compound of the formula (III) with a lower alkanol, R$^4$OH, or with the sodio derivative of a lower alkanol, phenol, substituted phenol, 5-indanol or naphthol, R$^4$OHa, followed by acidification, may be reacted (as such, or after conversion to a reactive derivative thereof, e.g. its acid chloride, an "activated" ester or a mixed anhydride) with a 7-($\alpha$-aminoarylacetamido)-4-carboxy-$\Delta^3$-cephem derivative of the formula (II) other than those in which R$^2$ is a hydroxyl group to produce a compound of the formula (I) in which R$^3$ represents an ester group, COOR$^4$ as hereinbefore defined, and X is defined as above in this method.

If the half-ester is to be reacted as such, this is conveniently effected in the presence of a dehydrating agent, e.g. dicyclohexylcarbodiimide or carbonyldiimidazole. In a typical procedure using carbonyldiimidazole, a solution of the half-ester in a suitable reaction-inert organic solvent, e.g. methylene chloride, is added to a cooled solution of the dehydrating agent in the same solvent, and after evolution of carbon dioxide has ceased the mixture is stirred at room temperature for a short time prior to addition of the $\Delta^3$-cephem derivative. Reaction may then be allowed to proceed during several hours at room temperature, preferably with continual stirring of the solution. Isolation of the product may be effected by evaporation of the reaction solution in vacuo to dryness, dissolution of the residue in water, extraction of the acidified aqueous solution into a water-immiscible organic solvent, e.g. ethyl acetate, and evaporation of the optionally washed and dried (e.g. with anhydrous magnesium sulphate) organic phase to dryness. The crude product thus produced may be purified, suitably by a standard crystallization technique.

The same reaction may alternatively be performed in aqueous solution using a water-soluble diimide as the dehydrating agent, of which a typical example is 1-(3-dimethylamino-n-propyl)-1-ethylcarbodiimide hydrochloride. In such a case, a mixture of the two reagents and the water-soluble diimide is added to an aqueous solvent, e.g. water itself or aqueous acetone, and the pH of the solution is adjusted to 5–6, e.g. by addition of hydrochloric acid, and maintained within that acidity range for several hours until stabilization, i.e. when no further quantity of mineral acid is required to maintain the acidity range. The product may then be extracted into a water-immiscible organic solvent, e.g. ethyl acetate, after acidifying the aqueous phase further, and isolating by evaporating to dryness the optionally washed and dried organic phase. Purification may then be effected by suitable means.

If it is desired to react the half-ester of the formula (VI) as its acid chloride with the 7-($\alpha$-aminoarylacetamido)-4-carboxy-$\Delta^3$-cephem derivative, the initial conversion to the acid chloride may be effected using a well-known standard technique for such a reaction, e.g. by maintaining a solution of the half-ester and a chlorinating agent such as oxalyl chloride or thionyl chloride in a suitable reaction-inert organic solvent such as benzene for several hours, preferably with stirring, at a suitable temperature, and isolating the crude product by evaporation of the reaction solution to dryness. Thereafter, the residue is conveniently reacted directly with the appropriate $\Delta^3$-cephem derivative, without purification, in a solvent, e.g. aqueous acetone, containing a base of the sort exemplified in Method (1) above. After sufficient reaction time, e.g. several hours, the product is conveniently isolated and purified by extracting it from an acidified aqueous solution into an organic phase, e.g. ethyl acetate, and then following a similar procedure to that described in Method (1) for the isolation and purification of the product.

The half-ester of the formula (VI) may be converted into an "activated" ester prior to reaction with the 7-($\alpha$-aminoarylacetamido)-4-carboxy-$\Delta^3$-cephem derivative using the preferred reagent N-hydroxysuccinimide in the presence of a dehydrating agent such as dicyclohexylcarbodiimide. The "activated" ester product of the formula:

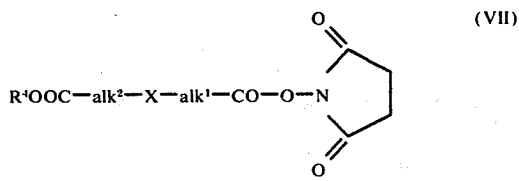
(VII)

is conveniently then reacted with the $\Delta^3$-cephem derivative in the reaction solution in which it has been formed, without isolation. In a typical procedure, a solution of the half-ester, N-hydroxysuccinimide and dehydrating agent in a reaction-inert organic solvent, e.g. tetrahydrofuran, is stirred for several hours at room temperature, after which the solid N,N'-dicyclohexylurea formed in the reaction may be removed, e.g. by filtration. To the solution containing the "activated" ester is then added a solution of the $\Delta^3$-cephem derivative, and reaction generally goes substantially to completion in the presence of a tertiary amine or inorganic base, as hereinbefore examplified and preferably with stirring during a period from 1 to 12 hours at room temperature. The solvent may then be removed, e.g. by evaporation in vacuo, and the residue dissolved in water, the aqueous solution then being acidified, extracted with a water-immiscible organic solvent, e.g. ethyl acetate, and the organic phase subjected to a similar procedure to that described in Method (1) for the isolation and purification of the product.

If the half-ester of the formula (VI) is to be converted to a mixed anhydride prior to reaction with the 7-($\alpha$-aminoarylacetamido)-4-carboxy-$\Delta^3$-cephem derivative, the initial conversion is suitably performed using a lower alkyl chloroformate, e.g. ethyl chloroformate. The reaction may suitably be effected by stirring a mixture of the half-ester, lower alkyl chloroformate and an equivalent quantity of a tertiary amine or inorganic base of the kind hereinbefore exemplified in a suitable solvent, e.g. methylene chloride, at a low temperature, e.g. 0° C., for a short time, e.g. ½ hour. Reaction with the Δ³-cephem derivative may then be effected, without the necessity to isolate the mixed anhydride, by adding a solution of the former in a suitable solvent, e.g. methylene chloride, containing an equivalent quantity of a base of the kind hereinbefore exemplified, to the reaction solution of the mixed anhydride, of the formula:

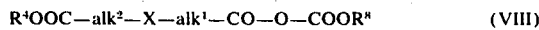

R⁴OOC—alk²—X—alk¹—CO—O—COOR⁸ (VIII)

wherein R⁸ represents a lower alkyl group, and stirring the reaction solution at room temperature for several hours. Isolation and purification of the product may then be effected by removing the reaction solvent, e.g. by evaporation in vacuo, dissolving the residue in water, acidifying the aqueous solution, extracting it with a water-immiscible organic solvent, e.g. ethyl acetate, and subjecting the organic phase to a similar procedure to that described in Method (1) in the final stages.

3. Compounds of the formula (I) in which R³ represents a carbamoyl group of the formula CONR⁵R⁶, as hereinbefore defined, R² is as already defined other than a hydroxyl group, and X is as already defined other than an unsubstituted imino group, —NH—, may be prepared by reacting a half-amide of the formula:

R⁵R⁶NCO—alk²—X—alk¹—COOH (IX)

optionally after conversion to its acid chloride, an "activated" ester or a mixed anhydride, with a 7-(α-aminoarylacetamido)-4-carboxy-Δ³-cephem derivative of the formula (II) other than those in which R² is a hydroxyl group. The half-amide of the formula (IX) may itself be prepared by reacting the appropriate amine, NHR⁵R⁶, with a cyclic acid anhydride of the formula (III) according to a conventional procedure.

The reaction between the half-amide or aforementioned derivative thereof and the Δ³-cephem derivative, and conversion of the half-amide into the appropriate derivative, where appropriate, prior to reaction with the Δ³-cephem derivative, may be achieved according to the analogous procedures given in Method (2), starting from the half-amide instead of the half-ester, and the isolation procedures may also be effected analogously.

4. Compounds of the formula (I) in which R² represents an N-pyridyl or azido group or any of the heterocyclic-thio groups specified hereinbefore may be prepared from the corresponding compounds in which R² represents an acetoxy group (cephalosporanic acid derivatives) by a displacement reaction with pyridine, sodium azide or the appropriate heterocyclic-thiol.

In the case of R² representing an azido or a heterocyclic-thio group, such a reaction may generally be performed by adding one of the latter reagents to a solution of the appropriate cephalosporanic acid derivative in an aqueous buffer solution, e.g. phosphate buffer, at a pH between 6 and 7.5, optionally containing a base, e.g. sodium bicarbonate, and heating the mixture within the temperature range 35°–70° C. for a period from 1 to 12 hours. The product may then be isolated by diluting the reaction mixture with water, overlayering the aqueous medium with a suitable water-immiscible organic solvent, e.g. ethyl acetate, acidifying the aqueous phase, e.g. to pH 2 by addition of sufficient hydrochloric acid, and thereby inducing extraction of the product into the organic phase, especially with shaking in addition, and thereafter separating, washing, e.g. with a saline solution, drying, e.g. with anhydrous magnesium sulphate, filtering and evaporating to dryness the organic phase. Purification of the crude product, if necessary, may be achieved by a standard recrystallization technique or by washing with a suitable solvent, e.g. diethyl ether.

In the case of R² representing an N-pyridyl group, the reaction may be performed by adding first pyridine, e.g. in 1 to 3 molar equivalents, and then potassium thiocyanate or iodide, e.g. in 1 to 10 molar equivalents, to a molar equivalent of the cephalosporanic acid derivative dissolved in water containing at least one molar equivalents of a base of the kind hereinbefore exemplified. To the mixture is then added sufficient phosphoric acid until pH 6 is attained, and the whole is suitably heated within the temperature range 25°–702 c. for a period from 6 to 48 hours. The product, either as the thiocyanate or iodide salt, may then be isolated by adjusting the pH of the solution to 2, e.g. by addition of 2N hydrochloric acid, and collecting the resulting precipitate by filtration. The betaine form of the product may be obtained by well-documented standard ion-exchange procedures.

5. Compounds of the formula (I) in which R³ represents an ester group, COOR⁴, or a carbamoyl group, CONR⁵R⁶, as hereinbefore defined, and X represents an oxygen or sulphur atom, or an imino group, —NR⁷—, as hereinbefore defined, may be prepared by reacting a 7-(α-aminoarylacetamido)-4-carboxy-Δ³-cephem derivative of the formula (II) other than those in which R² is a hydroxyl group to produce a compound of the formula (I) in which R³ represents an ester group, COOR⁴, as hereinbefore defined, with a chloroalkanoyl chloride of the formula:

Cl—alk¹—COCl (X)

and then reacting the product, of the formula:

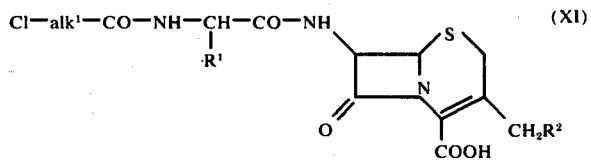

(XI)

first with sodium iodide to convert it to the corresponding iodo compound and then with, as appropriate, one of the compounds of formulae:

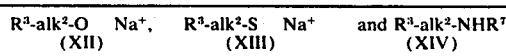

| R³-alk²-O Na⁺, | R³-alk²-S Na⁺ | and R³-alk²-NHR⁷ |
|---|---|---|
| (XII) | (XIII) | (XIV) | wherein R³ is as defined as above in this method.

The initial reaction may suitably be effected by maintaining the reactants, of which the acid chloride is preferably in slight excess, at a low temperature, e.g. within the range 0° C. to room temperature, in a reaction-inert organic solvent, e.g. chloroform, in the presence of a tertiary amine or inorganic base, as hereinbefore exemplified, for several hours, preferably with stirring. Isolation of the product, of the formula (XI), is suitably accomplished by removing the solvent from the reaction mixture, e.g. by evaporation in vacuo, dissolving the residue in an aqueous medium, e.g. water itself or a basic aqueous medium such as saturated aqueous sodium bicarbonate solution, extracting the subsequently acidified, e.g. to pH 2, aqueous phase with a water-immiscible organic solvent, e.g. ethyl acetate, and thereafter subjecting the organic phase to a similar procedure to that described in Method (1) for the isolation and, if necessary, purification of the product.

Reaction between the compound of the formula (XI) and sodium iodide may conveniently be accomplished by allowing a solution, e.g. acetone, of the two reagents in approximately equimolar proportions to stand in darkness for several hours at room temperature. Thereafter, that solvent may be replaced with a water-immiscible organic solvent, e.g. ethyl acetate, and the solution washed, e.g. with a saline solution, dried, e.g. over anhydrous magnesium sulphate, filtered and evaporated in vacuo to dryness.

The final stage is typically performed by dissolving the iodo compound in a suitable reaction-inert organic solvent, e.g. methylene chloride or dimethylformamide and adding, as appropriate, the sodium alcoholate [formula (XII)], sodium thiolate [formula (XIII)] or amine [formula (XIV)] in a slight excess, e.g. 10%. After stirring the mixture for several hours within the temperature range 20°-80° C., the solvent is removed, e.g. by evaporation in vacuo, and the residue is dissolved in a suitable waterimmiscible organic solvent, e.g. ethyl acetate. The solution may then be washed, e.g. with a saline solution, dried, e.g. over anhydrous magnesium sulphate, filtered and evaporated in vacuo to dryness, thus furnishing the desired product, which may be purified, if necessary, by a standard recrystallization technique or by washing in a suitable solvent, e.g. diethyl ether.

6. Compounds of the formula (I) in which $R^3$ and X represent any of the hereinbefore specified atoms or groups with the exception of a sulpho group and an unsubstituted imino group, —NH—, respectively, may be prepared by reacting a trimethylsilyl-protected α-aminoarylacetic acid, $R^1CH(NH_2)CO_2Si(CH_3)_3$, with one of the compounds of formulae:

  (XV)

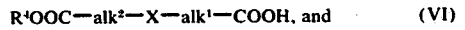  (VI)

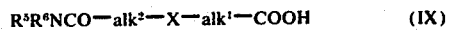  (IX)

wherein X is defined as above in this method, in each case either as such or having been converted to its acid chloride, an "activated" ester or a mixed anhydride, to produce a compound of the formula:

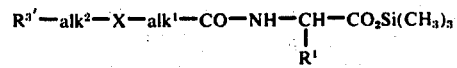

(XVI)

wherein $R^{3'}$ represents, as appropriate, one of the moieties $Ph_2CHOOC$, $R^4OOC$ and $R^5R^6NCO$, which is subsequently hydrolyzed to the corresponding α-aminoarylacetic acid derivative, of the formula:

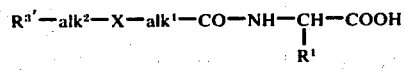

(XVII)

this then being converted to its functional equivalent as an acylating agent and reacted with a 7-amino-4-carboxy-Δ³-cephem derivative of the formula:

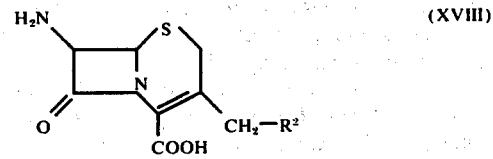

wherein $R^2$ is as defined for formula (I) other than hydroxyl to produce a compound of the formula:

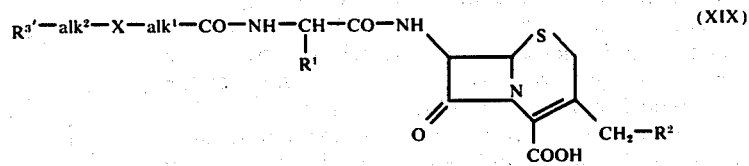

the latter, when $R^{3'}$ represents the carbobenzhydryloxy group, $Ph_2CHOOC$, finally being acidified to a compound of the formula (I) in which $R^3$ represents a carboxyl group.

The starting trimethylsilyl-protected α-amino-arylacetic acid may be prepared from the unprotected compound by reaction with an approximately equivalent quantity of a silylating agent, e.g. trimethylsilyl chloride, in the presence of a tertiary amine base, e.g. triethylamine, in solution in a suitable reaction-inert organic solvent, e.g. methylene chloride. For convenience, to this solution is added directly one of the compounds of the formulae (XV), (VI) and (IX), either as such together with a condensing agent, e.g. dicyclohexylcarbodiimide, or as an acid chloride, "activated" ester or mixed anhydride, prepared according to one of the procedures given in Method (2), and optionally in the reaction medium in which each was formed. The reaction to form the compound of the formula (XVI) may suitably be performed by stirring the mixture at room temperature for several hours, after which the mixture is filtered to remove any solids present, e.g. the dicyclohexylurea formed from dicyclohexylcarbodiimide present as a dehydrating agent either in this reaction or in the reaction to form an activated ester if used. Treatment of the filtrate with mineral acid, e.g. 10% hydrochloric acid, converts the product to a free acid by removing the trimethylsilyl protecting group, and the organic phase may then be washed, e.g. with saline solution, dried, e.g. with anhydrous magnesium sulphate, filtered, and evaporated in vacuo thus affording a compound of the formula (XVII).

Conversion of the latter compound to that of formula (XIX) is preferably achieved by first forming therefrom a mixed anhydride, e.g. with isovaleric or pivalic acid, and then reacting this product with the 7-amino-4-$\Delta^3$-cephem derivative of the formula (XVIII). The reactions are typically achieved by adding isovaleroyl or pivaloyl chloride, in slight excess, to a solution of the acid in a suitable reaction-inert organic solvent, e.g. tetrahydrofuran, in the presence of a tertiary amine base, e.g. triethylamine, at a low temperature, e.g. $-10°$ C. The mixture is then stirred, e.g. for ½ hour, to effect the converion to the mixed anhydride and added to a stirred solution of the 7-amino-4-carboxy-$\Delta^3$-cephem derivative of the formula (XVIII) in a suitable aqueous solvent, e.g. aqueous tetrahydrofuran. Reaction generally proceeds satisfactorily at room temperature during several hours, after which the product is extracted from the acidified reaction solution into a water-immiscible organic solvent, e.g. ethyl acetate, the organic phase then being washed, e.g. with saline solution, dried, e.g. over anhydrous magnesium sulphate, filtered and evaporated in vacuo. If the product is of the formula (XIX) wherein $R^{3'}$ represents one of the moieties $R^4OOC$ and $R^5R^6NCO$, it may be purified, if necessary, by recrystallization or washing in a suitable solvent, e.g. diethyl ether. Otherwise, being a compound of the formula (XIX) wherein $R^{3'}$ represents a carbobenzhydryloxy group, the latter may be removed by acidification, and the product purified as before. The acidification may be achieved, in a typical case, by adding trifluoroacetic acid (3 volumes) to a solution of the carbobenzhydryloxy derivative in anisole (1 volume) and allowing the mixture to stand at room temperature for several minutes. Isolation and purification of the product is then effected by removing the solvent by evaporation in vacuo, dissolving the residue in ethyl acetate, adding the solution slowly to a large volume of petroluem ether, and collecting the resulting preceipitate of the desired product by filtration.

7. All the compounds of the formula (I) in which X represents an unsubstituted imino group, $-NH-$, may be prepared according to Methods (1), (2), (3) and (6) given hereinbefore, starting in each case from one of the reagents of the formulae (III), (IV), (VI), (IX) and (XV) wherein the moiety X is replaced by $-NR^{7'}-$, in which $R^{7'}$ represents a suitable protecting group for an imino group, e.g. a tertiary-butyloxycarbonyl group. The procedures are performed similarly, and the final products of such procedures, all of the formula (I) wherein X is replaced by $-NR^{7'}-$, are subjected to a further reaction entailing the removal of the protecting group by conventional means.

In a typical case, the tertiary-butyloxycarbonyl group may be removed by stirring the appropriate compound in trifluoroacetic acid at 0°–25° C., and the deprotected product may then be isolated and purified by removing the excess acid, e.g. by evaporation in vacuo, and washing the residue in diethyl ether. However, when Method (6) is used to prepare a compound of the formula (I) in which $R^3$ represents a carboxyl group, the final acidification stage may also deprotect the protected amino group simultaneously, thus avoiding the necessity to perform an additional acidification reaction.

8. Salts of the compounds of the invention may be prepared, if desired, by standard techniques. For example, preparation of the sodium or potassium salt of a compound of the invention may be accomplished by dissolving the compound in a lower alkanol, e.g. methanol, cooling the resulting solution and adding a solution of the appropriate alkali metal acetate in the same solvent to the stirred organic solution. The reaction is in many cases effected by maintaining the reaction mixture for several hours at room temperature, and the salt may then be isolated by concentrating the reaction solution by partial evaporation in vacuo and adding the concentrate to a large volume of a suitable organic solvent, e.g. diethyl ether, thereby precipitating the salt. Purification may then be achieved by washing the salt in a suitable solvent, e.g. diethyl ether, and thereafter drying it, preferably in vacuo.

9. The compounds of the formula (I) in which $R^2$ is a hydroxy group may be prepared by the hydrolysis of the corresponding cephalosporin in which $R^2$ is an acetoxy group. Typically, the hydrolysis may be carried out in aqueous media at pH of from 5 to 8, using a wheat germ esterase or acetyl citrus esterase. The enzyme is aqueous solution is typically added to the sodium salt of the acetoxy-containing cephalosporin in water. The pH is rapidly adjusted to the desired value. The hydrolysis may then be effected by keeping the mixture at a suitable temperature, preferably between 20° and 45° C., by the addition of aqueous alkali until hydrolysis is complete. Completion of the hydrolysis can be determined by titration with alkali, or by chromatographic assay. The hydrolysis products may be recovered by conventional methods. Typically, the reaction mixture is overlayered with a water-immiscible solvent, e.g. ethyl acetate, the mixture cooled and the pH adjusted to a value of from 1.5 to 4.5. The insoluble protein may be removed by filtration. The separated organic layer may then be underlayered with water and the pH adjusted to a value of from 4.5 to 8.5. The aqueous extract may then be freeze-dried or concentrated in vacuo and the resultant sodium salt purified by recrystallization from a water-miscible solvent mixture, preferably a mixture of lower alcohols, e.g. methanol and isopropyl alcohol.

10. The compounds of the formula (I) in which R and $R^2$ taken together represent an oxygen atom, i.e. cephalosporins containing a lactone grouping, may be prepared by treating the corresponding derivative in which R and $R^2$ are each hydroxy with a mineral acid, e.g. 2N hydrochloric acid. Typically, the reaction is carried out in aqueous solution containing a water-miscible solvent, e.g. aqueous dioxan at a temperature of preferably from 5° to 50° C. for a period of several hours, e.g. ½ hour to 48 hours. The solution may then be concentrated in vacuo, and the precipitated product removed by filtration or centrifugation.

11. Compounds of the formula (I) in which $R^2$ is a carbamoyloxy group may be prepared by reacting the corresponding cephalosporin in which $R^2$ is a hydroxy group with a conventional protecting agent so as to protect the carboxyl group in the 4-position of the cephem nucleus, and, if present, the carboxyl group in the 7-side chain, and then reacting with an isocyanate and finally removing the protecting group or groups. A suitable protecting agent is diphenyldiazomethane which may be reacted with the unprotected cephalosporin in an inert solvent, e.g. ethyl acetate, typically at 10° to 45° C. for from ½ hour to 48 hours. The resultant mono- or di-ester may then be dissolved in an inert organic solvent, e.g. acetone, and then treated with trichloroacetyl isocyanate at preferably from 0° to 50° C. to give the corresponding 3-N-trichloro-acetylcarbamoyloxy-methyl derivative. Treatment of this derivative with acid, e.g. 0.1N HCl, or chromatography on silica gel, gives the mono- or bis- (depending on whether 7-side chain of the starting material contained a free carboxyl group) diphenyl methyl ester of the 3-carbamoyloxymethyl derivative. The ester group or groups may then be removed in a conventional manner, e.g. by the use of trifluoroacetic acid and aniaole at temperatures of up to 50° C.

The in vitro evaluation of the compounds of the invention as antibacterial agents was performed by determining the minimum inhibitory concentration (MIC) of the test compound in a suitable medium at which growth of the particular microorganism failed to occur. In practice, agar (brain/heart infusion agar) plates, each having incorporated therein the test compound at a particular concentration, were inoculated with a standard number of cells of the test microorganism and each plate was then incubated for 24 hours at 37° C. The plates were then observed for the presence or absence of the growth of bacteria and the appropriate MIC value noted. Microorganisms used in such tests and against which the compounds were effective included strains of Escherichia coli, Klebsiella pneumoniae, Proteus mirabilis, Pseudomonas aeruginosa, Staphylococcus aureus, Streptococcus pyogenes, Proteus vulgaris, Haemophilus influenzae and Enterobacter aerogenes, and Neisseria gonorrhea.

A selection of MIC values of many of the compounds hereinafter exemplified for activities against the various strains of microorganisms indicated is given in the following table:

pharmaceutical practice. For example, they may be administered orally in the form of tablets containing such excipients as starch or lactose, or in capsules wither alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

In treatment of bacterial infections in man, the compounds of this invention may be administered orally or parenterally, in accordance with conventional procedures for antibiotic administration, generally in an amount of from about 5 to 200 mg./kg./day and preferably about 5 to 20 mg./kg./day in divided dosage, e.g. three to four times a day. They may be administered in dosage units containing, for example, 125 to 500 mg. of the active ingredient with suitable physiologically acceptable carriers or excipients. The dosage units may be in the form of liquid preparations such as solutions or suspensions or as solids in tablets or capsules.

Thus, according to a yet further aspect, the invention provides a pharmaceutical composition comprising a compound of the formula (I) as previously defined and a pharmaceutically acceptable carrier. The compositions may preferably be in a form of a dosage unit containing from 125 to 500 mg. of the active cephalosporin.

The invention also provides a method of treating animals to cure them of diseases caused by gram-positive or gram-negative bacteria, which comprises admin-

| Example No. of Compound | Escherichia coli 51A266 | Pseudomonas aeruginosa 52A490 | Klebsiella pneumoniae 53A009 | Enterobacter aerogenes 55A004 | Proteus mirabilis 57C015 | Proteus vulgaris 57C060 | Staphylococcus aureus 01A005 | Streptococcus pyogenes 02C203 |
|---|---|---|---|---|---|---|---|---|
| 1 | 3.1 | 6.2 | 1.5 | 3.1 | 1.5 | 1.5 | 6.2 | 1.5 |
| 4 | 25 | 25 | 6.2 | 25 | 3.1 | 3.1 | 12.5 | 3.1 |
| 6 | 50 | 12.5 | 12.5 | 100 | 6.2 | 6.2 | 25 | 3.1 |
| 7 | 50 | 50 | 25 | 50 | 6.2 | 6.2 | 12.5 | 3.1 |
| 9 | 25 | 25 | 25 | 100 | 25 | 12.5 | 25 | 25 |
| 10 | 25 | 12.5 | 50 | 6.2 | 3.1 | 3.1 | 25 | 25 |
| 13 | 6.2 | 6.2 | 6.2 | 6.2 | 3.1 | 1.5 | 12.5 | 3.1 |
| 14 | 100 | 25 | 25 | 50 | 6.2 | 6.2 | 25 | 12.5 |
| 15 | 6.2 | 6.2 | 6.2 | 12.5 | 3.1 | 1.5 | 6.2 | 1.5 |
| 16 | 12.5 | 6.2 | 12.5 | 50 | 6.2 | 6.2 | 3.1 | 0.78 |
| 17 | 25 | — | 6.2 | 6.2 | 6.2 | 6.2 | 25 | 0.78 |
| 22 | 1.5 | 6.2 | 1.5 | 1.5 | 1.5 | 1.5 | 6.2 | 0.8 |
| 23 | 12.5 | — | 1.5 | 3.1 | 3.1 | 3.1 | 100 | 3.1 |
| 26 | 25 | 25 | 3.1 | 25 | 3.1 | 3.1 | 12.5 | 1.5 |
| 27 | 25 | 25 | 12.5 | 12.5 | 6.2 | 6.2 | 12.5 | 6.2 |
| 28 | 6.2 | 12.5 | 12.5 | 6.2 | 3.1 | 3.1 | 12.5 | 3.1 |
| 29 | 25 | 25 | 12.5 | 12.5 | 6.2 | 6.2 | 25 | 3.1 |
| 30 | 12.5 | 12.5 | 6.2 | 6.2 | 3.1 | 3.1 | 3.1 | 0.39 |
| 31 | 25 | 25 | 12.5 | 25 | 12.5 | 12.5 | 3.1 | 1.5 |
| 32 | 25 | 6.2 | 12.5 | 50 | 12.5 | 12.5 | 3.1 | 0.39 |
| 34 | 12.5 | 12.5 | 12.5 | 25 | 12.5 | 6.2 | 6.2 | 6.2 |
| 35 | 12.5 | 6.2 | 6.2 | 12.5 | 6.2 | 6.2 | 6.2 | 6.2 |
| 36 | 12.5 | 6.2 | 6.2 | 12.5 | 6.2 | 6.2 | 3.1 | 6.2 |
| 37 | 6.2 | 12.5 | 6.2 | 6.2 | 6.2 | 100 | 6.2 | 3.1 |
| 38 | 12.5 | 50 | 6.2 | 25 | 3.1 | 3.1 | 6.2 | 3.1 |
| 39 | 25 | 12.5 | 12.5 | 12.5 | 12.5 | 12.5 | 12.5 | 12.5 |
| 40 | 12.5 | 25 | 12.5 | 12.5 | 6.2 | 3.1 | 25 | 6.2 |
| 41 | 6.2 | 6.2 | 3.2 | 6.2 | 3.1 | 3.1 | 6.2 | 0.4 |
| 42 | 25 | 25 | 12.5 | 12.5 | 6.2 | 6.2 | 12.5 | 6.2 |
| 43 | 12.5 | 25 | 6.2 | 12.5 | 6.2 | 6.2 | 6.2 | 6.2 |

The compounds of the invention can be administered alone but will generally be administered in admixture with a pharmaceutical carrier selected with regard to the intended route of administration and standard istering to the animal an antibacterially effective amount of a compound of the formula (I).

The invention is illustrated by the following Examples.

EXAMPLE 1

A mixture of 7-D-(α-aminophenylacetamido)cephalosporanic acid (cephaloglycin) (228 g., 0.562 mole) and diglycolic anhydride (62.2 g., 0.562 mole) in acetone (3.3 l.) was stirred at room temperature for 1½ hours. After the removal by filtration of insoluble material, the filtrate was evaporated in vacuo at a temperature below 30° C., and the resulting gummy residue was stirred in a mixture of ethyl acetate (4.4 l.) and water (3.2 l.). The aqueous phase was separated and extracted with ethyl acetate (2.2 l.), and the separated organic phase was combined with the initial ethyl acetate solution, the organic solution then being dried over anhydrous magnesium sulphate, filtered and evaporated in vacuo, at a temperature below 30° C., to dryness.

Produced was a semi-solid foam (284.4 g.) which was shown from thin-layer-chromatographic and infra-red and nuclear magnetic resonance spectroscopic evidence to comprise substantially pure 7-D-(α-carboxymethoxyacetamido-phenylacetamido)cephalosporanic acid.

EXAMPLE 2

To a solution of the product of the previous Example is isopropanol (2.8 l.) was added a solution of anhydrous sodium acetate (45.9 g., 0.562 mole) in methanol (460 ml.), whereupon a bulky gelatinous precipitate formed. The suspension was stirred for 5 minutes to induce any further precipitation and then allowed to stand for 1 hour. The solid product was collected by filtration, washed with 1:6 methaol:isopropanol solution and then with isopropanol, and finally dried in vacuo at room temperature for several hours.

Produced was 244 g. of a solid which was shown from thin-layer-chromatographic and nuclear magnetic resonance spectroscopic evidence to comprise substantially pure sodium salt of 7-D-(α-carboxymethoxyacetamido-phenylacetamido)cephalosporanic acid.

EXAMPLES 3 TO 18

The following 7-aminocephalosporanic acid or 7-amino-3-desacetoxycephalosporanic acid derivatives were prepared by a similar procedure to that described in Example 1, starting from the appropriate 7-D-(α-aminophenylacetamido)cephalosporanic acid or corresponding 3-desacetoxy compound, and the appropriate cyclic anhydride of the formula (III) or (IV) herein. All the compounds were characterized by means of infrared and nuclear magnetic resonance spectroscopy.

| Example | $R^2$ | P | Q | $-alk^1-X-alk^2-R^3$ |
|---|---|---|---|---|
| 3 | H | H | H | $-CH_2-O-CH_2-COOH$ |
| 4 | $OCOCH_3$ | H | H | $-CH_2-S-CH_2-COOH$ |
| 5 | H | H | H | $-CH_2-S-CH_2-COOH$ |
| 6 | $OCOCH_3$ | H | H | $-CH_2CH_2COOH$ |
| 7 | $OCOCH_3$ | H | H | $-(CH_2)_3COOH$ |
| 8 | H | H | H | $-(CH_2)_3COOH$ |
| 9 | $OCOCH_3$ | H | H | $-CH(CH_3)-O-CH(CH_3)-COOH$ |
| 10 | $OCOCH_3$ | H | H | $-CH_2-S-CH_2-COOH$ ↓ O |
| 11 | H | H | H | $-CH_2-S-CH_2-COOH$ ↓ O |
| 12 | 2-methyl-1,3,4-thiadiazol-5-ylthio | H | H | $-CH_2-O-CH_2-COOH$ |
| 13 | $OCOCH_3$ | H | H | $-CH_2-N(CH_3)-CH_2-COOH$ |
| 14 | $OCOCH_3$ | H | H | $-CH_2CH_2SO_3H$ |
| 15 | $OCOCH_3$ | H | H | $-CH_2-N-CH_2-COOH$ <br> \| <br> $CH_2-CH=CH_2$ |
| 16 | $OCOCH_3$ | H | H | $-CH_2-N-CH_2-COOH$ <br> \| <br> $CH_2Ph$ |
| 17 | $OCOCH_3$ | HO | H | $-CH_2OCH_2-COOH$ |
| 18 | $OCOCH_3$ | HO | Cl | $-CH_2OCH_2-COOH$ |

EXAMPLE 19

To a stirred solution of cephaloglycin (2 g., 0.005 mole) in dimethylformamide (25 ml.) was added to a solution of adipic anhydride polymer (6.4 g., 0.05 mole) in dimethylformamide (30 ml.), and the mixture was stirred at room temperature for about 16 hours. The resulting solid was then filtered off, and the filtrate, a yellow solution, was poured into petroleum ether (60°–80° C., 500 ml.) with vigorous stirring. From the resulting solid lower layer the solvent was decanted, and the residue was then treated with 10% aqueous sodium bicarbonate solution with stirring. The remaining solid was removed by filtration, and the filtrate was acidified to pH 4.5 by cautious addition to dilute hydrochloric acid, and extracted with ethyl acetate. Evaporation of the organic phase in vacuo to dryness afforded a pale yellow oil which was found from nuclear magnetic resonance spectroscopic evidence to consist principally of adipic acid. The aqueous phase was acidified further to pH 1 and extracted with ethyl acetate, the isolated pale yellow solid (2.1 g.) from evaporation of the organic phase subsequently being shown to also contain a large proportion of acipic acid.

A portion (1.0 g.) of the yellow solid was dissolved in 10% aqueous sodium bicarbonate solution, and the solution was acidified in stages to pH 4.5, 4.0 and 3.3 by addition of the appropriate amount of N hydrochloric acid and extraction with ethyl acetate after each addition. The organic phases were evaporated to dryness at each stage and their contents investigated by nuclear magnetic resonance spectroscopy. It was found that each fraction contained a considerable proportion of adipic acid, and so was discarded. Finally, the aqueous solution was acidified to pH 2.0 and extracted with a mixture of ethyl acetate and chloroform. The separated organic phase was dried over anhydrous magnesium sulphate and evaporated in vacuo to dryness, affording a solid (250 mg.) containing, from nuclear magnetic resonance spectroscopic evidence, a trace of adipic acid and a major proportion of 7-D-(α-[5-carboxyvaleramido]phenylacetamido)cephalosporanic acid.

EXAMPLE 20

By a similar procedure to that described in Example 19, 7-D-(α-[5-carboxyvaleramido]phenylacetamido)-3-desacetoxycephalosporanic acid was prepared from 7-D-(α-aminophenylacetamido)-3-desacetoxycephalosporanic acid and adipic anhydride polymer, and characterized by means of infra-red and nuclear magnetic resonance spectoscopy.

EXAMPLE 21

A. To a mixture of iminodiacetic acid (13.3 g., 0.1 mole) and tertiarybutyloxycarbonyl azide (21.5 g., 0.15 mole) in 1:4 water:dioxane (125 ml.) at 60° C. was added 2N sodium hydroxide solution at the rate required to maintain the solution of pH 10.2. When the pH has stabilized at that value, the reaction mixture was cooled, extracted three times with diethyl ether in order to remove unreacted azide, and cooled to 0° C. Solid citric acid was added to the aqueous solution to bring it to pH 3, followed by sufficient sodium chloride to saturate it. The solution was then extracted three times with ethyl acetate and the combined organic phases were washed with water and dried over anhydrous magnesium sulphate. The white solid (13.0 g.), m.p. 124°–125° C., produced on evaporation of the ethyl acetate solution in vacuo to dryness, was characterized from infra-red and nuclear magnetic resonance spectroscopic evidence as N-(tertiary-butyloxycarbonyl)iminodiacetic acid.

B. A mixture of the product of (A) (2.0 g., 0.0086 mole) and acetic anhydride (25 ml.) was heated over a steam bath for 20 minutes. The resulting purple solution was evaporated in vacuo to an oil, and the latter was decolorized by dissolving it in ethyl acetate, shaking the solution with a little charcoal, removing the latter by filtration and evaporating the filtrate in vacuo, thereby affording a yellow oil. Warming of the latter under high vacuum caused it to crystallize as a pale yellow, hygroscopic solid, m.p. 65° C. The product was identified by infra-red spectroscopy as N-(tertiary-butyloxycarbonyl) iminodiacetic anhydride.

C. By a similar procedure to that described in Example 1, starting from the product of (B) and cephaloglycin, 7-D-(α-[N-carboxymethyl-N-{tertiary-butyloxycarbonyl} amino]acetamido-phenylacetamido)cephalosporanic acid was prepared, and characterized by means of infra-red and nuclear magnetic resonance spectroscopy.

D. To the product of (C) (1.5 g.) was added cooled trifluoroacetic acid at 0° C., and the mixture was stirred at room temperature for 45 minutes. The excess trifluoroacetic acid was then removed by evaporation in vacuo, and to the resulting solid residue was added diethyl ether. After the residue had been triturated, the clear upper ethereal layer was removed by decantation, and a fresh portion of diethyl ether was added to the suspension and further trituration performed. When the clear upper ethereal layer had been removed, the suspension was evaporated in vacuo to dryness, affording a product which was shown from thin-layer-chromatographic and infra-red and nuclear magnetic resonance spectroscopic evidence to comprise substantially pure 7-D-(α-[carboxymethylaminoacetamido]-phenylacetamido) cephalosporanic acid as its trifluoroacetic acid addition salt.

EXAMPLE 22

To a vigorously stirred suspension of the trifluoroacetic acid addition salt of 7-D-(α-aminophenylacetamido)-3-(1-methyl-1,2,3,4-tetrazol-5-ylthiomethyl)-Δ³-cephem-4-carboxylic acid (1.65 g., 0.0029 mole; prepared as described in British Pat. No. 1,283,811 and U.S. Pat. No. 3,641,021) in dry dimethylformamide (10 ml.) was added diglycolic anhydride (0.34 g., 0.0029 mole). The solid dissolved, affording a light brown solution, and after 30 minutes the solution was added to an equipart aqueous solution comprising saturated sodium chloride and saturated sodium bicarbonate solutions. After the mixed solution had been overlayered with ethyl acetate, sufficient 2N hydrochloric acid was added to bring the aqueous phase to pH 4, and the ethyl acetate phase (containing principally unchanged starting 7-amino-Δ³-cephem derivative) was removed from the previously well-shaken two-phase solution. A fresh quantity of ethyl acetate was added to the aqueous solution, and the latter was brought to pH 2 by addition of a further quantity of 2N hydrochloric acid. The two-phase solution was shaken to ensure sufficient extraction, and the ethyl acetate phase was then separated, washed with saturated aqueous sodium chloride solution, dried over anhydrous sodium sulphate, filtered and evaporated in vacuo to dryness, affording a gum.

Trituration of the crude product as a gum in diethyl ether afforded a buff-colored solid, which was collected by filtration and dried for several hours in vacuo. The solid (1.25 g.) was purified by first washing it with diethyl ether and then dissolving as much of it as possible in methanol, removing insoluble material by filtration, dripping the methanolic filtrate into diethyl ether, collecting the resulting precipitate by filtration and finally drying the solid for several hours in vacuo. Produced and characterized as such from infra-red and nuclear magnetic resonance spectroscopy was 7-D-(α-carboxymethoxyacetamido-phenylacetamido)-3-(1-methyl-1,2,3,4-tetrazol-5-ylthiomethyl)-Δ³-cephem-4-carboxylic acid.

EXAMPLES 23 AND 24

The following 7-aminocephalosporanic acid derivatives were prepared by a similar procedure to that described in Example 22, starting from the appropriate 7-D-(α-amino-[substituted phenyl]acetamido)-3-(1-methyl-1,2,3,4-tetrazol-5-ylthiomethyl)-Δ³-cephem-4-carboxylic acid and diglycolic anhydride:

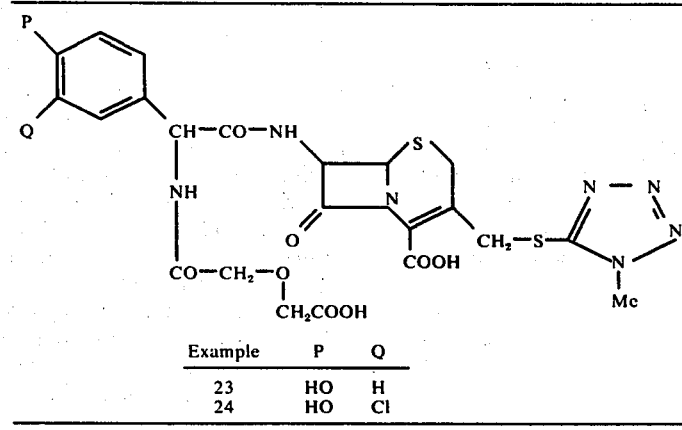

| Example | P | Q |
|---|---|---|
| 23 | HO | H |
| 24 | HO | Cl |

EXAMPLE 25

By a procedure similar to that described in Example 22, starting from the same cephalosporin starting material as Example 22, and N-methyl iminodiacetic acid anhydride, 7-D-(α-carboxymethyl [N-methyl-]aminoacetamidophenylacetamido)-3-(1-methyl-1,2,3,4-tetrazol-5-ylthiomethyl)-Δ³-cephem-4-carboxylic acid was prepared, and characterized by means of infra-red and nuclear magnetic resonance spectroscopy.

EXAMPLE 26

A. 5-Indanol (73.8 g., 0.55 mole) was added to a solution of sodium methoxide in methanol (prepared from 11.6 g., 0.5 mole of sodium and 400 ml. of dry methanol), and after the mixture had been allowed to stand at room temperature for 5 minutes the solvent was removed by evaporation in vacuo. The residue was dissolved in dry dimethylformamide (200 ml.) and the solution was evaporated in vacuo to dryness, thereby removing some moisture from the residue. To a solution of the residue in dry dimethylformamide (400 ml.) was added a solution of diglycolic anhydride (58 g., 0.5 ml.) in dry dimethylformamide (60 ml.), after which the mixture, whose temperature had risen to 70° C., was stirred for 3 hours. The solvent was then removed by reduced pressure evaporation to afford a solid, which was distributed between diethyl ether (150 ml.) and 2N hydrochloric acid (50 ml.), the separated ethereal phase then being washed with water (2 × 100 ml.) and extracted with saturated aqueous sodium bicarbonate solution. After the aqueous phase had been washed with diethyl ether (100 ml.), it was acidified with 2N hydrochloric acid and extracted with diethyl ether. The separated ethereal phase was washed with water, dried over anhydrous magnesium sulphate, filtered and evaporated in vacuo to dryness, the resulting solid then being recrystallized from a mixture of chloroform and petroleum ether (b.p. 60°–80° C.) to afford 54 g. of mono-5-indanyl diglycolate, m.p. 95°–98° C.

Analysis: Calc'd for $C_{13}H_{14}O_5$: C, 62.39; H, 5.64%. Found: C, 62.75; H, 5.80%

B. To a solution of a portion of the product of (A) (5 g., 0.02 mole) in dry benzene (50 ml.) was added oxalyl chloride (5 ml.) followed by one drop of dimethylformamide. When the ensuing evolution of carbon dioxide had ceased, the solution was left to stand at room temperature for an hour. The solvent was removed by evaporation in vacuo, and a solution of the residue in dry benzene was evaporated in vacuo, thereby effecting removal of some moisture from the acid chloride product.

The residue was dissolved in dry acetone (50 ml.), and a portion of this solution (13 ml.) was slowly added to a solution of cephaloglycin (2.0 g., 0.005 mole) in aqueous acetone (45 ml., containing 5 parts water to 4 parts acetone by volume) containing sodium bicarbonate (0.84 g., 0.01 mole). After the solution had been stirred at room temperature for 1½ hours, further quantities of sodium bicarbonate (0.42 g.) and aqueous acetone solution of cephaloglycin (13 ml.) were added, and stirring was continued for a further 2 hours. The solution was then filtered and evaporated in vacuo to dryness, the resulting gum subsequently being partitioned between aqueous and ethyl acetate phases. To the separated aqueous phase was added sufficient 2N hydrochloric acid to bring it to pH 2, and the solution was then extracted with ethyl acetate. The ethyl acetate phase was washed with water, dried over anhydrous magnesium sulphate, filtered and evaporated in vacuo to dryness, after which the residual solid was washed with dry diethyl ether and dried for several hours in vacuo. Infra-red and nuclear magnetic resonance spectroscopic evidence was consistent with the product (1.3 g.) being 7-D-(α-[5-indanyl]oxycarbonylmethoxyacetamido-phenylacetamido)cephalosporanic acid.

EXAMPLES 27 TO 29

The following 7-aminocephalosporanic acid derivatives were prepared by similar procedures to that described in Example 26 from cephaloglycin, oxalyl chloride, and the appropriate half-ester in place of mono-5-indanyl diglycolate. All the compounds were characterized by means of infra-red and nuclear magnetic resonance spectroscopy.

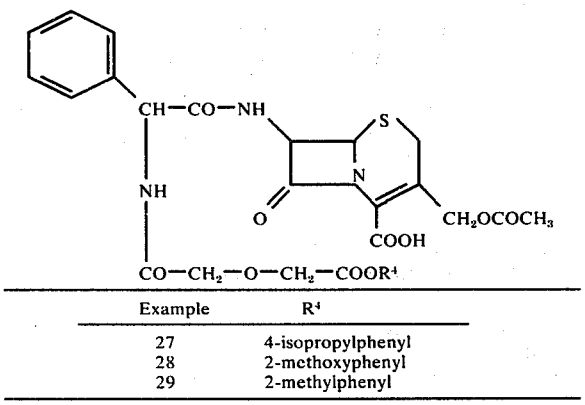

| Example | R⁴ |
|---|---|
| 27 | 4-isopropylphenyl |
| 28 | 2-methoxyphenyl |
| 29 | 2-methylphenyl |

EXAMPLE 30

A. A mixture of diglycolic anhydride (27.9 g.) and methanol (6.75 ml.) was heated in a steam bath for two hours, and the resulting clear liquid was then submitted to a reduced pressure distillation, the major quantity of distillate collected (8.5 g.) having a boiling point of 168°–172° C./12 mms mercury pressure and being monomethyl diglycolate.

B. A portion of the product of (A) (1.48 g., 0.01 mole) was dissolved in methylene chloride (5 ml.), and the solution was added to a solution of carbonyldiimidazole (1.62 g., 0.01 mole) in methylene chloride (25 ml.) at 10° C. Evolution of carbon dioxide occurred, after which the solution was stirred at room temperature for 30 minutes and then added to a solution of cephaloglycin (2 g., 0.005 mole) and triethylamine (1.5 g., 0.015 mole) in methylene chloride (100 ml.). The reaction solution was stirred at room temperature for 2 hours and then evaporated in vacuo to dryness, affording a gum.

A solution of the gum in water (50 ml.) was overlayered with ethyl acetate, sufficient 2N hydrochloric acid added to the aqueous phase to bring ot to pH 2, and the two-phase solution shaken vigorously for several minutes to effect sufficient extraction. The ethyl acetate phase was then separated, dried over anhydrous magnesium sulphate, filtered and evaporated in vacuo to afford a gum. The latter was dissolved in methylene chloride (20 ml.), and the solution slowly dripped into dry diethyl ether (400 ml.) with vigorous stirring. After decanting the volume of ether above the sediment and replacing it with a fresh quantity of dry diethyl ether, the solid was collected by filtration and dried in vacuo for several hours. Thin-layer-chromatographic and infra-red and nuclear magnetic resonance spectroscopic evidence was consistent with the product (0.84 g.) being substantially pure 7-D-(α-methoxycarbonylmethoxyacetamido-phenylacetamido)cephalosporanic acid.

EXAMPLE 31

By a similar procedure to that described in Example 30, 7-D-(α-[n-butyl]oxycarbonylmethoxyacetamido-phenylacetamido)cephalosporanic acid was prepared from cephaloglycin, carbonyldiimidazole, diglycolic anhydride and n-butanol in place of methanol. It was characterized by means of infra-red and nuclear magnetic resonance spectroscopy.

EXAMPLE 32

A mixture of cephaloglycin (2 g.) and N,N-diethylcarboxymethoxyacetamide (3.4 g.) was suspended in water (50 ml.) and the pH was adjusted to 7 by addition of 2N sodium hydroxide solution. To the suspension was added 1-ethyl-3-(3-dimethylaminopropyl)carbodiimide hydrochloride, and the pH of the solution was readjusted to 5.8 and kept thereat, by periodic addition of small quantities of 2N hydrochloric acid, for 2 hours, after which time the acidity had stabilized. A sufficient quantity of 2N sodium hydroxide solution was then added to neutralize the solution, and the latter was overlayered with ethyl acetate. Extraction into the organic layer was achieved by acidifying the lower aqueous layer to pH 2 and shaking the two-phase solution.

The organic phase was subsequently separated, washed with water, dried over anhydrous magnesium sulphate, filtered and evaporated in vacuo to dryness, affording a pale yellow solid. This was washed with dry diethyl ether and dried in vacuo for several hours. Produced and characterized as such from infra-red and nuclear magnetic resonance spectroscopy was 2.4 g. of 7-D-(α-[N,N-diethylcarbamoyl]methoxyacetamido-phenylacetamido)cephalosporanic acid.

EXAMPLE 33

To a stirred suspension of 7-D-(α-carboxymethoxyacetamido-phenylacetamido)cephalosporanic acid (1 g., 0.0019 mole; the product of Example 1), in phosphate buffer at pH 7.0 (15 ml.) was added anhydrous sodium bicarbonate (0.35 g.). When all the solid had dissolved, 5-mercapto-1-methyl-1,2,3,4-tetrazole (0.38 g., 0.0024 mole) was added and the mixture was heated in an oil bath at 60° C. for 6 hours.

The solution was then diluted to a volume of 100 ml. with water, overlayered with ethyl acetate and acidified to pH 2.0 with 2N hydrochloric acid. After the two-phase solution had been shaken vigorously for several minutes to effect sufficient extraction, the ethyl acetate phase was separated, washed with saturated aqueous sodium chloride solution, dried with anhydrous magnesium sulphate, filtered and evaporated in vacuo to dryness. The resulting off-white gum was dissolved in a small quantity of methanol, the solution was dripped into dry diethyl ether, and the resulting precipitate collected by filtration and dried for several hours in vacuo. Produced and characterized as such by infra-red and nuclear magnetic resonance spectroscopy was 7-D-(α-carbomethoxyacetamido-phenylacetamido)-3-(1-methyl-1,2,3,4-tetrazol-5-ylthiomethyl)-Δ³-cephem-4-carboxylic acid (0.35 g.). Comparsion of its infra-red and nuclear magnetic resonance spectra with those of the product of Example 22 confirmed its identity with the latter.

EXAMPLES 34 TO 42

The following 7-amino-3-substituted-cephalosporanic acid derivatives were prepared by similar procedures to that described in Example 33 from 7-D-(α-carboxymethoxyacetamido-phenylacetamido)cephalosporanic acid and the appropriate mercapto-substituted tetrazole, thiadiazole or other heterocyclic derivative. All the compounds were characterized by means of infra-red and nuclear magnetic resonance spectroscopy.

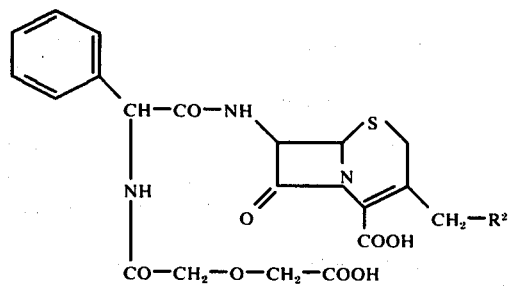

| Example | $R^2$ |
|---|---|
| 34 | 1-phenyl-1,2,3,4-tetrazol-5-ylthio |
| 35 | 1-(4-methoxyphenyl)-1,2,3,4-tetrazol-5-ylthio |
| 36 | 1-(4-chlorophenyl)-1,2,3,4-tetrazol-5-ylthio |
| 37 | 2-methyl-1,3,4-thiadiazol-5-ylthio |
| 38 | 4,6-dimethylpyrimidin-2-ylthio |
| 39 | 4,5-dimethylthiazol-2-ylthio |
| 40 | 1,3,5-triazin-2-ylthio |
| 41 | 1-benzyl-1,2,3,4-tetrazol-5-ylthio |
| 42 | pyrimidin-2-ylthio |

The compound of Example 37 is also the subject of Example 12.

EXAMPLE 43

To a stirred suspension of 7-D-(α-carboxymethoxyacetamido-phenylacetamido)cephalosporanic acid (1 g., 0.0019 mole), the product of Example 1) in phosphate buffer at pH 6 (30 ml.) was added anhydrous sodium bicarbonate (0.4 g.). When all the solid had dissolved, sodium azide (0.65 g., 0.01 mole) was added and the mixture was heated in a water bath at 50° C. for 16 hours.

The solution was then diluted to a volume of 100 ml. with water, overlayered with ethyl acetate, and acidified to pH 2 with 2N hydrochloric acid. After the two-phase solution had been shaken vigorously for several minutes to effect sufficient extraction, the ethyl acetate phase was separated, washed with saturated aqueous sodium chloride solution, dried with anhydrous magnesium sulphate, filtered and evaporated in vacuo to dryness. The resulting foam was triturated in diethyl ether to afford an off-white solid (0.52 g.) which was characterized by infra-red and nuclear magnetic resonance spectroscopy as 3-azidomethyl-7-D-(α-carboxymethoxyacetamido-phenylacetamido)-Δ³-cephem-4-carboxylic acid.

The following compounds are similarly prepared from the appropriate 7-D-(α-acylaminoarylacetamido)cephalosporanic acid derivatives:

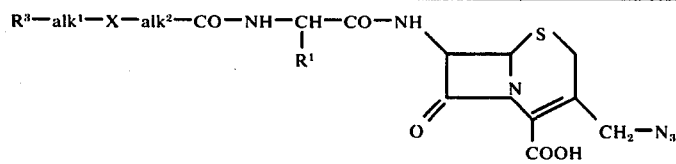

| $R^1$ | $alk^1$-X-$alk^2$-$R^3$ |
|---|---|
| 4-$HOC_6H_4$ | $-CH_2-O-CH_2-COOH$ |
| 4-$HOC_6H_4$ | $-CH_2-S-CH_2-COOH$ |
| 4-$HOC_6H_4$ | $-CH_2-O-CH_2-CON(C_2H_5)_2$ |
| 3-Cl-4-$HOC_6H_3$ | $-CH_2CH_2SO_3H$ |
| $C_6H_5$ | $-CH_2-SO_2-CH_2-COOH$ |
| $C_6H_5$ | $-(CH_2)_4-COOH$ |
| $C_6H_5$ | $-CH_2-N(CH_3)-CH_2COOH$ |
| 4-$ClC_6H_4$ | $-CH_2-O-CH_2-COOH$ |
| 4-$CH_3C_6H_4$ | $-CH_2-N(CH_2Ph)-CH_2-COOH$ |
| 4-$CF_3C_6H_4$ | $-CH_2-O-CH_2-COOH$ |
| 2-thienyl | $-CH_2-O-CH_2-COOH$ |
| 2-thienyl | $-CH_2CH_2-COOH$ |
| 3-thienyl | $-CH_2-S-CH_2-COOH$ |
| 2-furyl | $-CH_2CH_2-SO_3H$ |

EXAMPLE 44

The following compounds are prepared from the appropriate 7-D-(α-aminoarylacetamido)cephalosporanic acid, or corresponding 3-desacetoxy compound, or 3-heterocyclic thiomethyl compound.

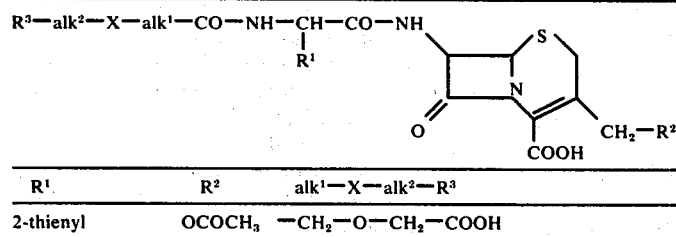

| $R^1$ | $R^2$ | $alk^1$—X—$alk^2$—$R^3$ |
|---|---|---|
| 2-thienyl | $OCOCH_3$ | $-CH_2-O-CH_2-COOH$ |

-continued

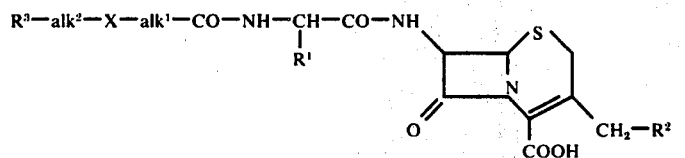

| R¹ | R² | alk¹—X—alk²—R³ |
|---|---|---|
| 2-thienyl | H | —CH₂—O—CH₂—COOH |
| 2-thienyl | H | —CH₂—S—CH₂—COOH |
| 2-thienyl | H | —CH₂CH₂COOH |
| 2-thienyl | OCOCH₃ | —(CH₂)₄—COOH |
| 2-thienyl | OCOCH₃ | —CH₂—SO—CH₂—COOH |
| 2-thienyl | OCOCH₃ | —CH₂—SO₂CH₂—COOH |
| 2-thienyl | H | —CH₂—N(CH₃)—CH₂—COOH |
| 2-thienyl | H | —CH₂—N(CH₂—CH=CH₂)—CH₂COOH |
| 2-thienyl | OCOCH₃ | —CH₂—O—CH₂—COOCH₃ |
| 2-thienyl | H | —(CH₂)₄—COOH |
| 2-thienyl | H | —CH₂—O—CH₂—COO—5-indanyl |
| 2-thienyl | OCOCH₃ | —CH₂—O—CH₂—COO-naphthyl |
| 2-thienyl | H | —CH₂—O—CH₂—CON(CH₃)₂ |
| 2-thienyl | OCOCH₃ | —CH₂—N(CH₂Ph)—CH₂—COOH |
| 3-thienyl | OCOCH₃ | —CH₂—O—CH₂—COO—(4—ClC₆H₄) |
| 3-thienyl | OCOCH₃ | —CH₂—S—CH₂—COOH |
| 3-thienyl | H | —(CH₂)₃—COOH |
| 3-thienyl | OCOCH₃ | —CH₂—N(CH₃)—CH₂COOH |
| 3-thienyl | H | —(CH₂)₄—COOCH₃ |
| 3-thienyl | H | —CH₂—SO₂—CH₂—COOH |
| 3-thienyl | H | —CH₂CH₂—SO₃H |
| 3-thienyl | OCOCH₃ | —CH₂—O—CH₂—COO—(2-CH₃O—C₆H₄) |
| 2-furyl | OCOCH₃ | —CH₂—OCH₂—COOH |
| 2-furyl | OCOCH₃ | —CH₂CH₂—COOH |
| 2-furyl | OCOCH₃ | —CH₂CH₂—SO₃H |
| 2-furyl | H | —CH₂—S—CH₂—COOH |
| 2-furyl | H | —CH₂—N(CH₂—CH=CH₂)CH₂—COOH |
| 2-furyl | H | —CH₂—O—CH₂—COO—(n-C₄H₉) |
| 2-furyl | OCOCH₃ | —(CH₂)₄—COOCH₃ |
| 4-ClC₆H₄ | OCOCH₃ | —CH₂—O—CH₂—COO—(3-CF₃C₆H₄) |
| 3-ClC₆H₄ | OCOCH₃ | —CH₂—S—CH₂—COOH |
| 3-IC₆H₄ | H | —CH₂—O—CH₂—COO—(4-t-C₄H₉C₆H₄) |
| 4-FC₆H₄ | H | —CH₂CH₂SO₃H |
| 3-BrC₆H₄ | OCOCH₃ | —CH₂—N(C₆H₁₃)—CH₂COOH |
| 3,4-(CH₃O)₂C₆H₃ | OCOCH₃ | —CH₂—O—CH₂—COOH |
| 4-CH₃OC₆H₄ | OCOCH₃ | —(CH₂)₄—COOH |
| 4-CH₃C₆H₄ | OCOCH₃ | —CH₂—N(CH₂Ph)—CH₂—COOH |
| 4-CF₃C₆H₄ | OCOCH₃ | —CH₂—O—CH₂—COOH |
| 4-FC₆H₄ | H | —CH₂—O—CH₂—COO—(5-indanyl) |
| 3-HOC₆H₄ | OCOCH₃ | —(CH₂)₄—COOH |
| 4-HOC₆H₄ | OCOCH₃ | —CH₂—S—CH₂—COOH |
| 4-HOC₆H₄ | OCOCH₃ | —CH₂—O—CH₂—CON(C₂H₅)₂ |
| 3-Cl-4-HOC₆H₃ | OCOCH₃ | —CH₂CH₂—SO₃H |
| 2-ClC₆H₄ | H | —CH₂—O—CH₂—CON(C₆H₁₃)₂ |
| C₆H₅ | H | —CH₂—N(n-C₃H₇)—CH₂—COOH |

EXAMPLE 45

The following 7-amino-3-substituted cephalosporanic acid derivatives are prepared by similar procedures to that described in Example 33 from appropriate reactants.

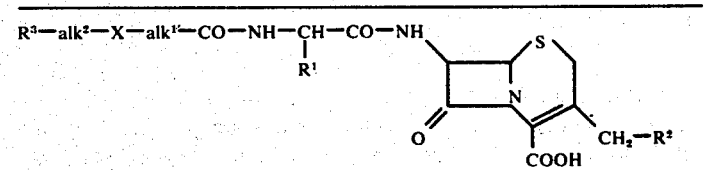

| R¹ | R² | —alk¹—X—alk²—R³ |
|---|---|---|
| 2-thienyl | 1-methyl-1,2,3,4-tetrazol-5-ylthio | —CH₂—CO—CH₂—COOH |
| 2-thienyl | 2-methyl-1,3,4-thiadiazol-5-ylthio | —CH₂—CO—CH₂—COOH |
| 2-thienyl | pyrimidin-2-ylthio | —CH₂CH₂—COOH |
| 2-thienyl | 4,5-dimethyl-thiazol-2-ylthio | —CH₂N(CH₃)—CH₂—COOH |
| 3-thienyl | 1-methyl-1,2,3,4-tetrazol-5-ylthio | —CH₂—O—CH₂—COOH |
| 3-thienyl | 1-phenyl-1,2,3,4-tetrazol-5-ylthio | —CH₂—S—CH₂—COOH |
| 3-thienyl | 4,6-dimethylpyrimidin-2-ylthio | —(CH₂)₃—COOH |
| 3-thienyl | 1,3,5-triazin-2-ylthio | —CH₂—O—CH₂—COOH |
| 2-furyl | 1-methyl-1,2,3,4- | —CH₂—O—CH₂—COOH |

-continued

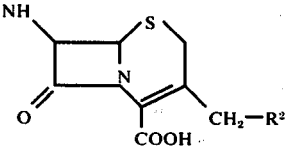

| R¹ | R² | —alk¹—X—alk²—R³ |
|---|---|---|
| 2-furyl | tetrazol-5-ylthio 1-(4-chlorophenyl)-1,2,3,4-tetrazol-5-ylthio | —CH$_2$—O—CH$_2$—COOH |
| 2-furyl | 1-benzyl-1,2,3,4-tetrazol-5-ylthio | —CH$_2$—S—CH$_2$—COOH |
| 2-furyl | pyrimidin-2-ylthio | —CH$_2$CH$_2$—SO$_3$H |
| C$_6$H$_5$ | 2-methyl-1,3,4-oxadiazol-5-ylthio | —CH$_2$CH$_2$COOH |

EXAMPLE 46

To 5 g. of 7-D-(α-carboxymethoxyacetamido-phenylacetamido)cephalosporanic acid sodium salt, dissolved in 250 ml. water and adjusted to pH 7 by addition of 2N aqueous hydroxide solution, was added 1.5 g. of a wheat germ esterase (Lipase from Wheat Germ Type 1, Sigma Chemical Co., St. Louis, Mo., U.S.A.) dissolved in 50 ml. water. The pH was continually re-adjusted to 7 by addition of 2N sodium hydroxide and the mixture stirred at room temperature (20° C.) for 5 hours, by which time hydrolysis was found to be complete, as shown by thin-layer-chromatography. The product was recovered by saturating the solution with sodium chloride, contacting with 250 ml. ethyl acetate, adjusting the pH of the aqueous phase to 2 with 2N aqueous hydrochloric acid solution, cooling to 0° C., filtering the 2-phase system through "Hi-Flo", separating the organic layer, washing the latter with brine and then with water, contacting it with 150 ml. water, adjusting the pH of the aqueous layer to 5.5 with 2N sodium hydroxide, separating the aqueous layer and freeze-drying the latter to give 2.5 g. of a buff, fluffy solid. The product was recrystallized from methanol-/isopropanol and shown to be 7-D-(α-carboxymethoxyacetamido-phenylacetamido)-3-hydroxymethyl-Δ³-cephem-4-carboxylic acid sodium salt, identified by nuclear magnetic resonance and infra-red spectrography and by thin-layer-chromatography.

EXAMPLE 47

The procedure of Example 46 is repeated, but using as starting materials the sodium salts of the cephalosporanic acid derivaties of Examples 4, 6, 7, 9, 10, 13-19 and 21, and those compounds of Example 44 in which R² is OCOCH$_3$ and R³ is COOH or SO$_3$H, thereby yielding the corresponding 3-hydroxymethyl-Δ³-cephem-4-carboxylic acids as sodium salts.

EXAMPLE 48

The procedure of Example 46 and 47 is repeated, but using acetyl citrus esterase extracted from orange peel by known methods (*Arch. Biochem.*, 1947, 15, 415) instead of wheat germ esterase, and the same results are achieved.

What is claimed is:
1. A compound for the formula:

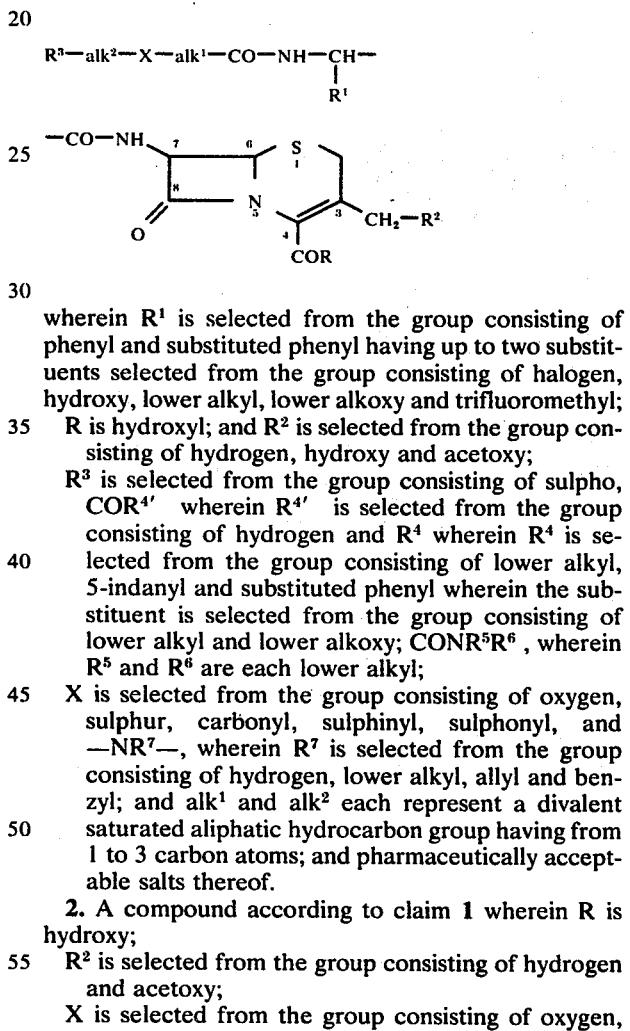

wherein R¹ is selected from the group consisting of phenyl and substituted phenyl having up to two substituents selected from the group consisting of halogen, hydroxy, lower alkyl, lower alkoxy and trifluoromethyl; R is hydroxyl; and R² is selected from the group consisting of hydrogen, hydroxy and acetoxy; R³ is selected from the group consisting of sulpho, COR⁴' wherein R⁴' is selected from the group consisting of hydrogen and R⁴ wherein R⁴ is selected from the group consisting of lower alkyl, 5-indanyl and substituted phenyl wherein the substituent is selected from the group consisting of lower alkyl and lower alkoxy; CONR⁵R⁶, wherein R⁵ and R⁶ are each lower alkyl; X is selected from the group consisting of oxygen, sulphur, carbonyl, sulphinyl, sulphonyl, and —NR⁷—, wherein R⁷ is selected from the group consisting of hydrogen, lower alkyl, allyl and benzyl; and alk¹ and alk² each represent a divalent saturated aliphatic hydrocarbon group having from 1 to 3 carbon atoms; and pharmaceutically acceptable salts thereof.

2. A compound according to claim 1 wherein R is hydroxy; R² is selected from the group consisting of hydrogen and acetoxy; X is selected from the group consisting of oxygen, sulphur, sulphinyl, sulphonyl and —NR⁷—, wherein R⁷ is selected from the group consisting of hydrogen, lower alkyl and benzyl.

3. A compound according to claim 2, wherein R¹ is phenyl or substituted phenyl; R² is acetoxy; R³ is -COOR⁴'; X is oxygen; and alk¹ and alk² are each methylene.

4. A compound according to claim 3 wherein R¹ is p-hydroxyphenyl.

5. A compound according to claim 3, wherein R³, wherein R¹ is m-chloro-p-hydroxyphenyl.

6. 7-D-(α-Carboxymethoxyacetamido-phenylacetamido)cephalosporanic acid, a compound according to claim 3 wherein R is hydroxyl; $R^1$ is phenyl; $R^2$ is acetoxy; each of $alk^1$ and $alk^1$ is methylene; X is oxygen and $R^3$ is carboxy.

7. 7-D-(α-Carboxymethoxyacetamido-phenylacetamido)-3-(1-methyl-1,2,3,4-tetrazol-5-ylthiomethyl)-Δ³-cephem-4-carboxylic acid, a compound according to claim 3 wherein R is hydroxyl; $R^1$ is phenyl; $R^2$ is 1-methyl-1,2,3,4-tetrazol-5-ylthiomethyl; each of $alk^1$ and $alk^2$ is methylene; X is oxygen and $R^3$ is carboxy.

8. 7-D-(α-Carboxymethoxyacetamido-[p-hydroxyphenyl]acetamido)-cephalosporanic acid, a compound according to claim 4 wherein R is hydroxyl; $R^2$ is acetoxy; each of $alk^1$ and $alk^2$ is methylene; X is oxygen and $R^3$ is carboxy.

9. 7-D-(α-Carboxymethoxyyacetamido-[m-chloro-p-hydroxyphenyl]-acetamido)cephalosporanic acid, a compound according to claim 5 wherein R is hydroxyl; $R^2$ is acetoxy; each of $alk^1$ and $alk^2$ is methylene; X is oxygen and $R^3$ is carboxy.

10. 7-D(α-[5-Indanyl]oxycarbonylmethoxyacetamido-phenylacetamido)-cephalosporanic acid, a compound according to claim 3 wherein R is hydroxyl; $R^1$ is phenyl; $R^2$ is acetoxy; each of $alk^1$ and $alk^2$ is methylene; X is oxygen and $R^3$ is 5-indanyloxycarbonyl.

11. 7-D-(α-[4-Isopropylphenyl]oxycarbonylmethoxyacetamido-phenylacetamido)cephalosporanic acid, a compound according to claim 3 wherein R is hydroxyl; $R^1$ is phenyl; $R^2$ is acetoxy; each of $alk^1$ and $alk^2$ is methylene; X is oxygen and $R^3$ is 4-isopropylphenyloxycarbonyl.

12. 7-D-(α-[2-methoxyphenyl]oxycarbonylmethoxyacetamido-phenylacetamido)cephalosporanic acid, a compound according to claim 3 wherein R is hydroxyl; $R^1$ is phenyl; $R^2$ is acetoxy; each of $alk^1$ and $alk^2$ is methylene; X is oxygen and $R^3$ is 2-methoxyphenyloxycarbonyl.

13. 7-D-(α-[2-methylphenyl]oxycarbonylmethoxyacetamido-phenylacetamido)cephalosporanic acid, a compound according to claim 3 wherein R is hydroxyl; $R^1$ is phenyl; $R^2$ is acetoxy; each of $alk^1$ and $alk^2$ is methylene; X is oxygen and $R^3$ is 2-methylphenyloxycarbonyl.

14. 7-D-(α-[n-butyl]oxycarbonylmethoxyacetamido-phenylacetamido)-celphalosporanic acid, a compound according to claim 3 wherein R is hydroxyl; $R^1$ is phenyl; $R^2$ is acetoxy; each of $alk^1$ and $alk^2$ is methylene; X is oxygen and $R^3$ is n-butyloxycarbonyl.

15. A pharmaceutical composition comprising a compound according to claim 1 and a pharmaceutically carrier.

16. A pharmaceutical composition comprising a compound according to claim 2 and a pharmaceutically acceptable carrier.

17. A composition according to claim 15 in the form of a dosage unit containing from 125 to 500 mg. of the compound.

18. A method of treating animals to cure them of diseases caused by gram-positive or gram-negative bacteria which comprises administering to the animal an antibacterially effective amount of a compound according to claim 1.

* * * * *